(12) United States Patent
Xin et al.

(10) Patent No.: US 6,897,215 B1
(45) Date of Patent: May 24, 2005

(54) COMPOUNDS HAVING 5-HT$_6$ RECEPTOR ANTAGONIST ACTIVITY

(75) Inventors: Tao Xin, Ontario (CA); Methvin Isaac, Ontario (CA); Abdelmalik Slassi, Ontario (CA)

(73) Assignee: NPS Allelix Corp., Mississauga (CA)

( * ) Notice: Subject to any disclaimer, the term of this patent is extended or adjusted under 35 U.S.C. 154(b) by 61 days.

(21) Appl. No.: 10/111,404

(22) PCT Filed: Nov. 4, 2000

(86) PCT No.: PCT/IB00/01595
§ 371 (c)(1),
(2), (4) Date: Jul. 19, 2002

(87) PCT Pub. No.: WO01/32660
PCT Pub. Date: May 10, 2001

Related U.S. Application Data

(60) Provisional application No. 60/163,785, filed on Nov. 5, 1999.

(51) Int. Cl.[7] ............... A61K 31/4985; A61K 31/437; C07D 487/04
(52) U.S. Cl. ............ 514/249; 514/299; 544/349; 546/112
(58) Field of Search ............ 544/349; 546/112; 514/249, 299

(56) References Cited

U.S. PATENT DOCUMENTS 6,251,893 B1 * 6/2001 Maddaford et al. .... 514/214.01

OTHER PUBLICATIONS

Robichaud et al. in Annual Reports in Medicinal Chemistry, vol. 35, p. 11–20 (2000).*
Isaac M et al: "6–bicyclopiperazinyl–1–arylsulfonylindole s and 6–bicyclopiperidinyl–1–arylsulfonylindoles derivatives as novel, potent, and selective 5–HT6 receptor antagonists" Bioorganic & Medicinal Chemistry Letters, Oxford, GB, vol. 10, No. 15, Aug. 7, 2000, pp. 1719–1721, XP004213231 ISSN: 0960–894X the whole document.

Ward R P et al: "Localization of Serotonin Subtype 6 Receptor Messenger RNA in the Rat Brain by in situ Hybridization Histochemistry" Neuroscience, New York, NY, US, vol. 64, No. 4, 1995, pp. 1105–1111, XP000943569 ISSN: 0306–4522 cited in the application p. 1107, right-–hand column –p. 1110, right–hand column.

Hoyer D and Martin G: "5–HT receptor classification and nomenclature: towards a harmonization with the human genome" Neuropharmacology, GB, Pergamon Press, Oxford, No. 36, Apr. 1, 1997, pp. 419–428, XPOO2075372 ISSN: 0028–3908 cited in the application table 1.

* cited by examiner

*Primary Examiner*—Emily Bernhardt
(74) *Attorney, Agent, or Firm*—Rothwell, Figg, Ernst & Manbeck, P.C.

(57) ABSTRACT

Novel 6-bicyclopiperazinyl-1-arylsulfonylindole and 6-bicyclopiperidinyl-1-arylsulfonylindole compounds are disclosed which are useful as 5-HT$_6$ receptor antagonists in the treatment of central nervous system disorders such as schizophrenia, depression, ADHD, and cognition and memory dysfunction The compounds are Formula I

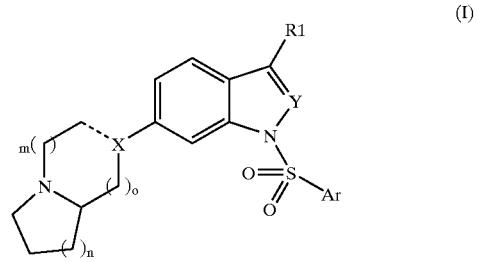

wherein: R1 is H or $C_{1-4}$ alkyl; X is CH, —C—OR3, =C, or —N and Y is C-R2 or N; R3 is H or —C(O)-R4; R4 is H or a labile prodrug group; n is 1 or 2; m and o are, independently, 0, 1, or 2 with the proviso that m+o is 1 or 2; and Ar is an aryl or heteroaryl group optionally substituted with 1–3 substitutents.

23 Claims, No Drawings

COMPOUNDS HAVING 5-HT$_6$ RECEPTOR ANTAGONIST ACTIVITY

CROSS-REFERENCE TO RELATED APPLICATION

This application is a National Stage entry of International Application No. PCT/IB00/01595, filed Nov. 4, 2000. This nonprovisional application claims the benefit of U.S. Provisional Application No. 60/163,785, filed Nov. 5, 1999.

FIELD OF THE INVENTION

This invention relates to indole compounds having affinity for the serotonin 5-HT$_6$ receptor, to pharmaceutical compositions containing them and to their medical use, particularly in the treatment of CNS conditions.

BACKGROUND OF THE INVENTION

The human 5-hydroxytryptamine-6 (5-HT$_6$) receptor, one of the most recently cloned serotonergic receptors, is a 440-amino acid polypeptide with seven transmembrane spanning domains typical of the G-protein-coupled receptors. It is one of the 14 receptors that mediate the effects of the neurotransmitter 5-hydroxytryptamine (5-HT, serotonin) (Hoyer et al, Neuropharmacology, 1997,36:419). Within the transmembrane region, the human 5-HT$_6$ receptor shows about 30–40% homology to other human 5-HT receptors and is found to be positively coupled to adenylyl cyclase.

The prominent localization of 5-HT$_6$ receptor mRNA in the nucleus accumbens, striatum, olfactory tubercle, substantia nigra, and hippocampus of the brain (Ward et al, Neuroscience, 1995, 64:1105) together with its high affinity for several therapeutically important antipsychotics and antidepressants, suggest a possible role for this receptor in the treatment of schizophrenia and depression. In fact, the prototypic atypical antipsychotic agent clozapine exhibits greater affinity for the 5-HT$_6$ receptor than for any other receptor subtype (Monsma et al, J. Pharmacol. Exp. Ther., 1994, 268:1403).

Although the 5-HT$_6$ receptor has a distinct pharmacological profile, in vivo investigation of receptor function has been hindered by the lack of selective agonists and antagonists. Recent experiments demonstrated that chronic intracerebroventricular treatment with an antisense oligonucleotide, directed at 5-HT$_6$ receptor mRNA, elicited a behavioral syndrome in rats consisting of yawning, stretching, and chewing. This syndrome in the antisense-treated rats was dose-dependently antagonized by atropine (a muscarinic antagonist), implicating 5-HT$_6$ receptor in the control of cholinergic neurotransmission. Therefore 5-HT$_6$ receptor antagonists may be useful for the treatment of memory dysfunction (Bourson et al, J. Pharmacol. Exp. Ther., 1995, 274:173), and to treat other CNS disorders.

It is an object of the present invention to provide compounds having 5-HT$_6$ receptor antagonist activity. It is a further object of the present invention to provide compounds that are selective and/or potent with respect to their binding at the 5-HT$_6$ receptor.

SUMMARY OF THE INVENTION

In accordance with the present invention, there are provided novel compounds, typically in the form of 6-bicyclopiperazinyl-1-arylsulfonylindole and 6-bicyclopiperidinyl 1-arylsulfonylindole derivatives, of the Formula I, or a salt, solvate, or prodrug thereof:

Formula I wherein:
R1 is H or C$_{1-4}$alkyl;
... X is —CH, —C—O-R3, =C, or —N;
... Y is —CH—R2, =C—R2, =N or —NR2
R2 is H or C$_{1-4}$alkyl;
R3 is H, or —C(O)-R4
R4 is H or a labile prodrug group
n is 1, 2, 3 or 4;
m and o are, independently, 0, 1, 2, 3 or 4 with the proviso that m+o is 1, 2, 3, or 4;
and Ar is an aryl or heteroaryl group optionally substituted with 1-3 substituents.

In accordance with another aspect of the present invention, there are provided pharmaceutical compositions comprising a therapeutically effective amount of a compound of Formula 1, or a salt, solvate, hydrate or prodrug thereof and a pharmaceutically acceptable carrier.

In accordance with other aspects, the present invention provides a method useful for the treatment of a medical condition for which a 5-HT$_6$ receptor antagonist is indicated, comprising the step of administering to a subject afflicted with said condition, a pharmaceutical composition comprising a compound of Formula I.

In accordance with another aspect of the present invention, there is provided a process for preparing a compound of Formula 1, in accordance with methods herein described.

These and other aspects of the present invention are now described in further detail.

DETAILED DESCRIPTION OF THE INVENTION

As used herein, the term "aryl" refers to a carbocyclic aromatic group selected from phenyl and naphthyl.

The term "heteroaryl" refers to an aryl group containing from 1 to 3 heteroatoms selected from O, N and S, and includes pyridyl, thienyl, quinolinyl, pyrimidyl, furyl, thiazolyl, oxazolyl, imidazolyl and the like.

The aryl and heteroaryl groups are optionally substituted by 1, 2 or 3 independently selected substituents which include C$_{1-4}$alkoxy, C$_{1-4}$alkyl, halo, nitro, trifluoromethyl, trifluoromethoxy, 1,2-alkylenedioxy, C$_{1-4}$alkylcarbonyl, C$_{1-4}$alkoxycarbonyl and C$_{1-4}$alkylS-.

In connection with those substituents, the term "C$_{1-4}$alkyl" means straight and branched chain alkyl radicals containing from one to four carbon atoms and includes methyl, ethyl, propyl, isopropyl, t-butyl and the like. Similarly, the terms C$_{1-4}$ alkylthio and C$_{1-4}$alkylcarbonyl refer to C$_{1-4}$alkyl groups in which there is a thio group or a carbonyl group bridging the C$_{1-4}$alkyl group to the node at which that substituent is substituted.

The term "C$_{1-4}$alkoxy" as used herein means straight and branched chain alkoxy radicals containing from one to four carbon atoms and includes methoxy, ethoxy, propyloxy, isopropyloxy, t-butoxy and the like. Similarly, the term $C_{1-4}$alkyloxycarbonyl refers to $C_{1-4}$ alkoxy group in which there is a carbonyl group bridging the substituent to the node at which the substitution occurs.

The term "1,2-alkylenedioxy" as used herein means "—O—$(CH_2)_n$—O—" wherein n is 1 or 2, attached to adjacent nodes of an aryl or heteroaryl ring.

The term "halo" as used herein means halogen and includes fluoro, chloro, bromo and the like.

The term leaving group (LG), as used herein with reference to chemical synthetic schemes, refers to a chemical group that is displaced in a chemical reaction, and the choice of leaving will depend on the nature of the reaction and the intended displacement. For instance, in scheme I shown herein, a leaving group suitable under those reaction conditions is halo and typically bromo.

The term "labile prodrug group" refers to a chemical moiety that is cleavable under conditions encountered following administration to the subject receiving the compound. Such compounds will convert in vivo to form the corresponding carboxyl moiety or in some instances, to form the hydroxyl moiety. Such conversion can be effected, for instance, by endogenuous enzymes including esterases, and the labile prodrug group therefore can be any group that is cleaved by those endogenous enzymes, including for instance alkyl groups.

In embodiments of the present invention, the group Y is selected desirably from =N, and =C-R2 wherein R2 is desirably H.

In other embodiments of the invention, the group R1 is H.

In still other embodiments of the invention, m, n and o are selected to form a bicyclic ring system of the type 5,5-, 5,6-, 5,7-, 5,8-, 6,5-, 6,6-, 6,7-, 6,8-, 7,5-, 7,6-, 7,7-, 7,8-, 8,5-, 8,6-, 8,7, and 8,8. Desirably, n is 1 or 2, and m and o are 0, 1 or 2. Preferably, m and o are each 1. In particular embodiments, m, n and o are selected to form a ring system which is 5,6-, 6,5- or 6,6-.

In other embodiments of the present invention, X is —CH, C—O—R3, or =C, and n is 1 or 2, and thereby to form either a 6,5-bicyclopiperidine ring or a 6,6 bicyclopiperidine ring, respectively.

In other embodiments, X is N and n is 1 or 2, and m and o are each 1, thereby to form either a 6,5-bicyclopiperazine ring or a 6,6-bicyclopiperazine ring, respectively.

In a preferred embodiment, n is 1.

In certain embodiments of the present invention, the compounds of Formula I are those in which Ar is an aryl group selected desirably from phenyl and naphthyl, including 1-naphthyl and 2-naphthyl that are either unsubstituted or substituted by one or two substituents. Specific substituents include $C_{1-4}$alkyl, particularly including methyl and halo, particularly including chloro and fluoro. Thus, in embodiments, Ar is 2-, 3- or 4-substituted phenyl, or 2,3-, 2,4- or 3,4-disubstituted phenyl. In specific embodiments of the invention, compounds of the present invention are those in which Ar is selected from 1-naphthyl, 2-naphthyl, phenyl, 4-methyl-phenyl, and 2,4-dihalo-phenyl, including 2,4-difluoro-phenyl. In a preferred embodiment, Ar is a naphthyl group, and particularly 1-naphthyl.

In a particularly preferred embodiment, m, n and o are each I and Ar is 1-napthyl.

In specific embodiments of the invention, the compounds of Formula 1 include:

6-[6,5-Bicyclopiperazinyl]-1-[1-naphthylenesulphonyl]indole;

6-[6,5-Bicyclopiperazinyl]-1-[toluenesulphonyl]indole;
6-[6,6-Bicyclopiperazinyl]-1-[1-naphthylenesulphonyl]indole;
6-[6,6-Bicyclopiperazinyl]-1-[p-toluenesulphonyl]indole;
6-[6,6-Bicyclopiperazinyl]-1-[2-naphthylenesulphonyl]indole;
6-[6,5-Bicyclopiperazinyl]-1-[2,4-difluorobenzenesulphonyl]indole;
6-[6,6-Bicyclopiperazinyl]-1-[bezenesulphonyl]indole;
6-[6,6-Bicyclopiperazinyl]-1-[o-toluenesulphonyl]indole;
6-[(8a-R,S)-1,2,3,5,6,8a-Hexahydroindolizin-7-yl]-1-naphthylsulfonyl-indole;
6-[(7-R,S)(8a-R,S)Octahydroindolizin-7-yl]-1-naphthylsulfonyl-indole; and
6[(7-R,S)(8a-R,S)-7-hydroxyoctahydroindolizin-7-yl-1-(4-methylphenylsulfonyl)indole.

In preferred embodiments of the present invention, the compounds include:

6-[6,5-Bicyclopiperazinyl]-1-[1-naphthylenesulphonyl]indole;
6-(6,6-Bicyclopiperazinyl]-[1-naphthylenesulphonyl]indole;
6-[(8a-R,S)-1,2,3,5,6,8a-Hexahydroindolizin-7-yl]-1-naphthylsulfonyl-indole; and
6-[(7-R,S)(8a-R,S)-Octahydroindolizin-7-yl]-1-naphthylsulfonyl-indole.

The compounds of the present invention are useful in the form of pharmaceutically acceptable salts, and as solvates and prodrugs.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts: can exist in either a hydrated, solvated or substantially anhydrous form. In general the acid addition salts of these compounds are more soluble in water and various hydrophilic organic solvents, and generally demonstrate higher melting points in comparison to their free base forms.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia The selection of the appropriate salt may be important so that an ester functionality elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol and the like.

The present compounds include any of their stereoisomeric forms, and racemates. The term "stereoisomers" is a general term for all isomers of the individual molecules that differ only in the orientation of their atoms in space. It includes mirror image isomers (enantiomers), geometric (cistrans) isomers and isomers of compounds with more than one chiral centre that are not mirror images of one another (diastereomers).

The present compounds are useful also in their "prodrugs" form. In general, such prodrugs will be functional derivatives of the compounds of Formula I which are readily convertible in vivo into the required compound of Formula L Conventional procedures for the selection and preparation of suitable prodrug derivatives are described, for example, in "Design of Prodrugs" ed. H. Bundgaard, Elsevier, 1985.

In accordance with other aspects of the invention, the compounds of the present invention can be prepared by processes analogous to those established in the art. The 6& bicyclopiperazinyl-1-arylsulfonylindoles, in which X is N and n, m, o, R1, Y and Ar are as defined above, can be prepared by the reaction illustrated below as Scheme I:

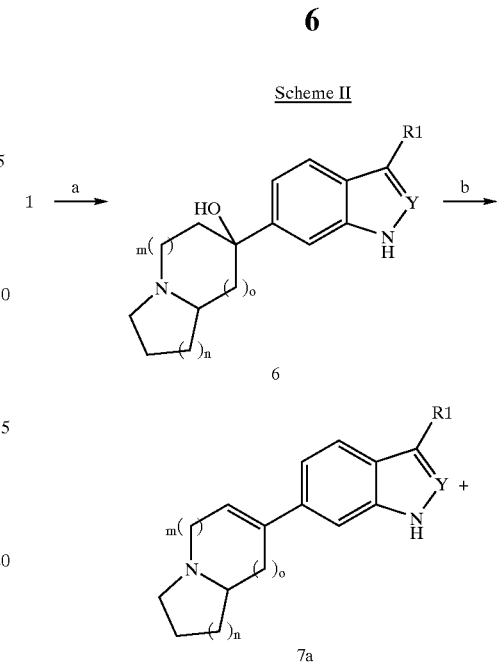

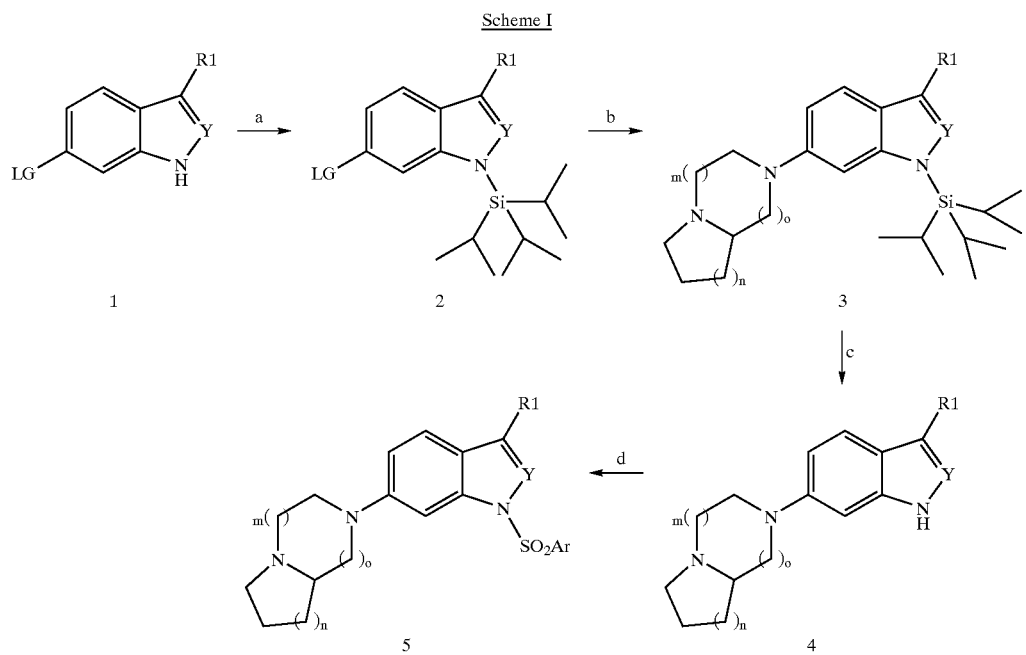

(a) NaH, TIPS-Cl, DMF, 0° C.; (b) bicyclopiperazine, NaOt-Bu, Pd(OAc)$_2$, t-Bu$_3$P, Xylene, 120° C.; (c) TBAF, THF; (d) NaHMDS, ArSO$_2$Cl, THF.

N-silyiation of 6-bromoindole or indazole 1 with triisopropylsilyl chloride (TIPS-Cl) yields 2, which is subjected to the conditions of metal-catalyzed aryl amination (Nishayama, M. et al; Tetrahedron Lett. 1998, 39, 617–620) to give 3. Subsequent desilylation of 3 affords 4, which is then sulfonylated to give 5.

The corresponding 6-piperidinyl-1-arylsulfonylindoles, or indazole in which X is C and n, m, o, R1, Y and Ar are as defined above, can be prepared by the reaction illustrated below as Scheme II:

-continued

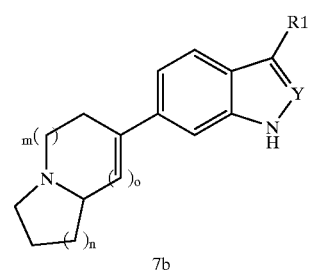

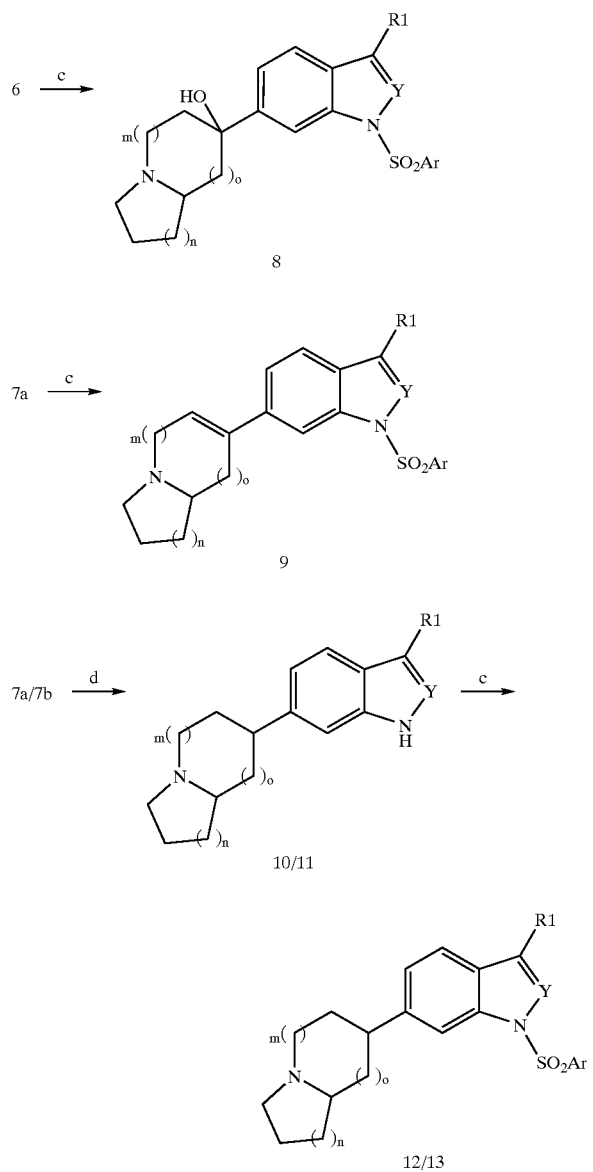

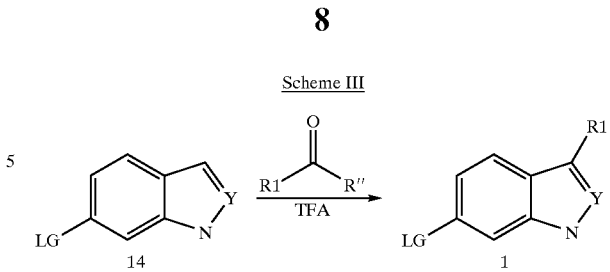

Scheme III

In the case where Y is N, compound 1 is made by the following procedure.

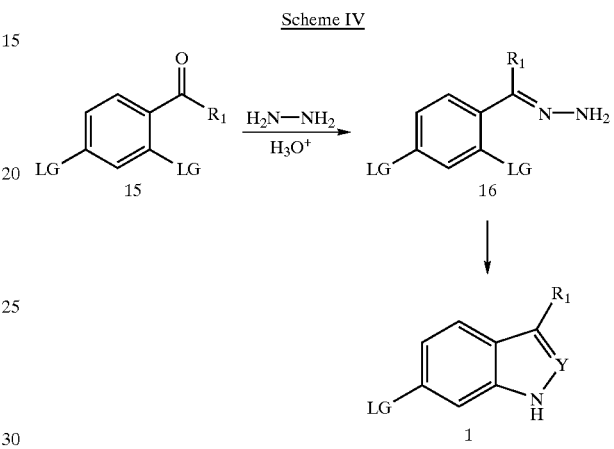

Scheme IV

The substituted phenone 15 is treated with hydrazine and acid to yeild the intermediate hydrazone, 16, which cyclizes to give the substituted indazole 1.

The present compounds are useful as pharmaceuticals for the treatment of various conditions in which the use of a 5-HT$_6$ receptor antagonist is indicated, such as in the treatment of central nervous system disturbances such as psychosis, schizophrenia, manic depression, depression, neurological disturbances, memory disturbances. Parkinsonism, amylotrophic lateral sclerosis, Alzheimer's disease, Attention deficit hyperactivity disorder (ADHD) and Huntington's disease.

The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The terms "treat", "treating" and "treatment" refer to alleviation of symptoms, elimination of the causation of the symptoms either on a temporary or permanent basis, or the prevention or slowing of the appearance of symptoms of the named disorder or condition.

Thus, in another of its aspects, the present invention provides a method for treating medical conditions for which a 5-HT$_6$ receptor antagonist is indicated, which comprises the step of administering to the patient a therapeutically effective amount of a compound of Formula I, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or (a) KH, t-BuLi, 9, THF, −78° C.; (b) TFA, F; (c) NaHMDS, ArSO$_2$Cl, THF; (d) H$_2$, Pd/C, MeOH.

The indole or indazole 1 is coupled to bicyclopiperidone (King et. al, *J. Med. Chem.*, 31, 9, 1988, 1708–1712 and *J. Chem. Soc. Perkin Trans.* 1,1986, 447–-454) to give the carbinol 6. Compound 6 is then ed with trifluoroacetic acid to effect the elimination to alkenes 7a and 7b. Both intermediate 6 and 7a are subjected to aryl sulfonylation to give 8 and 9, respectively. Palladium catalyzed hydrogenation of 7a and/or 7b gives two diastereoisomers 10 and 11, which are easily separated by column chromatography. Arylsulfonylation of the diastereoisomers gives 12 and 13 (designated as the more polar and less polar isomers, respectively).

In the case where Y is CR, The variable R1 is incorporated by reaction of indole or indazole 14 with the corresponding ketone and trifluoroacetic acid to give the substituted indole I as shown in Scheme III hydrate thereof in an amount effective to treat the target indication. The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant that can be a compressed gas such as compressed air or an organic propellant such as fluorachlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit dosages, i.e. therapeutically effective amounts, can be determined during clinical trials designed appropriately for each of the conditions for which administration of a chosen compound is indicated and will of course vary depending on the desired clinical endpoint. In general, the term "therapeutically effective amount" means an amount of the compound which is effective in treating, e.g., reducing the severity or duration of, the named disorder or condition or of any symptom thereof, and includes particularly an amount effective to antagonize the $5HT_6$ receptor. Such amounts are revealed as an amount which when administered to a subject over the course of an appropriate treatment regimen results in reduction of the level or magnitude of an effect normally elicited by triggering of the endogenous $5\text{-}HT_6$ receptor. Each dosage unit for oral administration may contain, for instance, from 0.01 to 500 mg/kg (and for parenteral administration may contain from 0.1 to 50 mg) of a compound of Formula I, or a pharmaceutically acceptable salt thereof calculated as the free base, and will be administered in a frequency appropriate for initial and maintenance treatments. For laboratory use, the present compounds can be stored in packaged form for reconstitution and use.

In another embodiment of the invention, the present compounds can be used to distinguish $5\text{-}HT_6$ receptors from other receptor subtypes, for example glutamate or opioid receptors, within a population of receptors, and in particular to distinguish between the $5\text{-}HT_6$ and other 5-HT receptor subtypes. The latter can be achieved by incubating preparations of the $5\text{-}HT_6$ receptor and one of the other 5-HT receptor subtypes (for example $5\text{-}HT_{2A}$ and $5\text{-}HT_7$) with a $5\text{-}HT_6$-selective compound of the invention and then incubating the resulting preparation with a radiolabeled serotonin receptor ligand, for example [$^3$H]-serotonin. The $5\text{-}HT_6$ receptors are then distinguished by determining the difference in membrane-bound activity, with the $5\text{-}HT_6$ receptor exhibiting lesser radioactivity, i.e., lesser [$^3$H]-serotonin binding, than the other 5-HT receptor subtype.

In another embodiment of the invention, the compound is provided in labeled form, such as radiolabeled form, e.g. labeled by incorporation within its structure $^3$H or $^{14}$C or by conjugation to $^{251}$I. In another aspect of the invention, the compounds in labeled form can be used to identify $5\text{-}HT_6$ receptor ligands by techniques common in the art. This can be achieved by incubating the receptor or tissue in the presence of a ligand candidate and then incubating the resulting preparation with an equimolar amount of radiolabeled compound of the invention. $5\text{-}HT_6$ receptor ligands are thus revealed as those that are not significantly displaced by the radiolabeled compound of the present invention. Alternatively, $5\text{-}HT_6$ receptor ligand candidates may be identified by first incubating a radiolabeled form of a compound of the invention then incubating the resulting preparation in the presence of the candidate ligand. A more potent $5\text{-}HT_6$ receptor ligand will, at equimolar concentration, displace the radiolabeled compound of the invention.

EXAMPLES

In the examples which follow, reference is made to the process schemes I and II described hereinabove Example 1

(a) General Procedure for the Synthesis of 6-Bromo-1-triisoproysilylindole (1->2):

A solution of 6-Bromoindole (1.96 g, 10 mmol) in DMF (5 ml) was added to a suspension of NaH (264 mg, 11 mmol) in DMF (15 ml) at 0° C. The mixture was allowed to stir at this temperature for 15 min after which triisopropylsilyl chloride (2.10 g, 11 mmol) was added dropwise. The mixture was then stirred at room temperature for 2 hrs. The reaction was then poured into ice-cold water followed by extraction with ethyl acetate (2×50 ml). The organic extract was washed with brine, and dried over $Na_2SO_4$ (anhydrous). The organic layer was concentrated in vacuo and purified by flash column chromatography giving 2.4 g (68%) of product as a white solid.

In a like manner the compound 6-bromo-1-triisopropylindazole may be prepared from 6-bromo-indazole by the conditions described above.

General Procedure for the Synthesis of 6-Bromo-1-trimethylsilylethoxymethylindole:

A solution of 6-Bromoindole (2.8 g, 14.4 mmol) in DMF (5 ml) was added to a suspension of NaH (375 mg, 15.6 mmol) in DMF (15 ml) at 0° C. The mixture was allowed to stir at this temperature for 15 min after which trimethylsilylethoxymethylchloride (2.4 g, 14.4 mmol) was added dropwise. The mixture was then stirred at room temperature for 2 hrs. The reaction was then poured into ice-cold water followed by extraction with ethyl acetate (2×50 ml). The organic extract was washed with brine, and dried over $Na_2SO_4$ (anhydrous). The organic layer was concentrated in vacuo and purified by flash column chromatography giving 3.9 g (83%) of product as a colourless oil.

In a like manner the compound 6-bromo-1-trimethylsilylethoxymethylindazole is prepared from 6-bromo-indazole by the conditions described above.

Example 2

General Procedure for the Amination of 6-Bromo-N-Protectedindole (2->3)

To a mixture of the N-protected 6-bromo indole produced as described in example 1 (1 eqv.), piperazine (6 eqv.) and sodium t-butoxide (1.4 eqv.) in xylene was added $Pd(OAc)_2$ and $P(t-Bu)_3$ (P/Pd=4). The mixture was heated at 120° C. overnight. The reaction was then poured into ice-cold water followed by extraction with ethyl acetate (2×50 ml). The organic extract was washed with brine, and dried over $Na_2SO_4$ (anhydrous). The organic layer was concentrated in vacuo and purified by flash column chromatography. By this process, the following intermediates were obtained:

(a) 6-[6,5-bicyclopiperazinyl]-1-trimethylsilylethoxymethylindole (270 mg of a orange oil 36% yield) from 6-bromo-1-trimethylsilylethoxymethylindole (example 1(b)) (652 mg, 2.0 mmol); and (b) 6-[6,6-Bicyclopiperazinyl]-1-triisopropylsilylindole (308 mg of an light brown, 75% yield) from 6-bromo-1-triisopropylsilylindole (example 1 (a)) (351 mg, 1.0 mmol).

In a like manner the following compounds are made from 1 equivalent of 6-bromo-1-trimethylsilylethoxymethylindole, and 6 equivalents of the corresponding bicyclopiperazine by the method described above.

(c) 6-(6,7-bicyclopiperazinyl)1-trimethylsilylethoxymethylindole
(d) 6-(6,8-bicyclopiperazinyl)-1-trimethylsilylethoxymethylindole
(e) 6-(7,5-bicyclopiperazinyl)-1-trimethylsilylethoxymethylindole
(f) 6-(7,6 bicyclopiperazinyl)-1-trimethylsilylethoxymethylindole
(g) 6-(7,7-bicyclopiperazinyl)-1-trimethylsilylethoxymethylindole
(h) 6-(7,8-bicyclopiperazinyl)-1-trimethylsilylethoxymethylindole
(i) o-(8,5-bicyclopiperazinyl)1-trimethylsilylethoxymethylindole
(j) 6-(8,6-bicyclopiperazinyl)-1-trimethylsilylethoxymethylindole
(k) 6-(8,7-bicyclopiperazinyl)-1-trimethylsilylethoxymethylindole
(l) 6-(8,8 bicyclopiperazinyl)-1-trimethylsilylethoxymethylindole In a like manner, the corresponding indazole compounds are made from the appropriate n-protected indazole from example 1.

Example 3

General Procedure for the Synthesis of 6-bicyclopiperazinyl-indole:

To a solution of the indole prepared as described above in Examples 2(a) and 2(b) (1 eqv.) in THF was added dropwise, tetrabutylammonium fluoride (1 eqv). The mixture was allowed to stir at this temperature for 30 min. The solvent was removed in vacuo, and water was added The crude aqueous mixture was then sonicated to give a solid that was filtered. By this process, the following intermediates were obtained:

(a) 6-[6,5-Bicyclopiperazinyl]indole (150 mg as a pale yellow solid, 94% yield); and
(b) 6-[6,6-Bicyclopiperazinyl]indole (150 mg as a beige solid, 63% yield)

In a like manner the following compounds are prepared from the corresponding N-protected indole deprotected by the procedure described above:

(c) 6-(6,7-bicyclopiperazinyl)-1H-indole
(d) 6-(6,8-bicyclopiperazinyl)-1H-indole
(e) 6-(7,5-bicyclopiperazinyl)-1H-indole
(f) 6-(7,6-bicyclopiperazinyl)-1H-indole
(g) 6-(7,7-bicyclopiperazinyl)-1H-indole
(h) 6-(7,8-bicyclopiperazinyl)1H-indole
(i) 6-(8,5-bicyclopiperazinyl)-1H-indole
(j) 6-(8,6-bicyclopiperazinyl)-1H-indole
(k) 6-(8,7-bicyclopiperazinyl)1H-indole
(l) 6-(8,8-bicyclopiperazinyl)-1H-indole In a like manner the corresponding indazole compounds are prepared by deprotection of the N-protected indazoles described in example 2.

Example 4

General Procedure for the Aryl Sulphonylation of 6-bicyclopiperazinyl-indole:

To a solution of the indole of example 3 (1 eqv.) in THF (2 ml) was added dropwise, NaHMDS (1.1 eqv). The mixture was allowed to stir at room temperature for 15 min. after which the aryl sulphonyl chloride (1.1 eqv) was added. The reaction was then poured into ice-cold water followed by extraction with $CH_2Cl_2$ (2×5 ml). The organic extract was washed with brine, and dried over $Na_2SO_4$ (anhydrous). The organic layer was concentrated in vacuo and purified by flash column chromatography. By this procedure, the following compounds of the present invention were obtained:

(a) 6-[6,5-Bicyclopiperazinyl]-1-[1-naphthylenesulphonyl] indole (15.3 mg, 70%)
(b) 6-[6,5-Bicyclopiperazinyl]-1-[toluenesulphonyl]indole (5 mg, 40%)
(c) 6[6,6-Bicyclopiperazinyl]-1-[1-naphthylenesulphonyl] indole (7 mg, 60%)
(d) 6-[6,6-Bicyclopiperazinyl]-1-[p-toluenesulphonyl] indole (10.5 mg, 98%)
(e) o-[6,6-Bicyclopiperazinyl]-1-[2-naphthylenesulphonyl] indole (11 mg, 95%)
(f) 6-[6,5-Bicyclopiperazinyl]-1-[2,4-difluorobenzenesulphonyl]indole (11 mg, 100/o)
(g) 6-[6,6-Bicyclopiperazinyl]-1-[bezenesulphonyl]indole (6.1 mg, 59%), and (h) 6[6,6-Bicyclopiperazinyl]-1-[o-toluenesulphonyl]indole (10 mg, 94%)

In a like manner the following compounds are made from the corresponding intermediate of example 3 and benzene sulphonyl chloride by the conditions described above.
(i) 6-[6,7-bicyclopiperazinyl]-1-[benzenesulphonyl]indole
(j) 6-[7,5-bicyclopiperazinyl]-1-[benzenesulphonyl]indole
(k) 6-[7,5-bicyclopiperazinyl]-1-[benzenesulphonyl]indole
(l) 6-[7,7-bicyclopiperazinyl]-1-[benzenesulphonyl]indole
(m) 6[7,8-bicyclopiperazinyl]-1-[benzenesulphonyl]indole
(n) 6-[8,5-bicyclopiperazinyl]-1-[benzenesulphonyl]indole
(o) 6-[8,5-bicyclopiperazinyl]-1-[benzenesulphonyl]indole
(p) 6-[8,7-bicyclopiperazinyl]-1-[benzenesulphonyl]indole
(q) 6-[8,8-bicyclopiperazinyl]-1-[benzenesulphonyl]indole In a like manner, the corresponding indazole compounds are prepared from the corresponding bicyclopiperazinyl-1H-indazoles from example 3, treated with an arylsulphonyl-chloride as described in example 4.

Example 5

Synthesis of Corresponding Piperidines

In the manner illustrated in Scheme II, the corresponding piperidines were also prepared:
A) Conversion of 1->6
(a) 6-[(7-R,S)(8a-R,S7-hydroxyoctahydroindolizin-7-yl]-1H-indole To the suspension of KH (0.289 g, 7.2 mmoles) in ThF(5 ml), 6-bromoindole (1.2 g, 6 mmoles) in 1 ml of THF was added dropwise at —10° C., and kept stirring at this temperature for 20 mins until no $H_2$ released. The reaction mixture was cooled to -78° C. with acetone and dry ice bath, the 1.7 M t-BuLi (8.82 ml, 15 mmoles) was added slowly, and stirred for another 30 mins. After 4-bicyclopiperidone (1.67 g. 1.2 mmoles) was added to the reaction mixture at -78° C. for another 30 mins, the reaction mixture was quenched by a mixture of dichloromethane (50 mil) and pH 7 buffer (50 ml), the insolubles were removed by filtration, CR2Cl2 layer was washed by water and brine, dried and concentrated. The residue was mixed with hexanes and filtered, yielding 0.52 g of 6-[(7-R,S)(8a-RS)-7-hydroxyoctahydroindolizin-7-yl]-1H-indole as a white powder (6, 33.1%).

In a like manner the following compounds are prepared:
(b) 6-[1-hydroxyhexahydro-1H-pyrrolizine-1-ol-yl]-1H-indole
(c) 6-[2-hydroxyoctahydro-2H-quinolizine-6-yl]-1H-indole
(d) 6-[9-hydroxydecahydropyrido(1,2-a) azepine-6-yl]-1H-indole
B) conversion of 6->8
(a) 6-[(7-R,S)(8a-R,S)-7-hydroxyoctahydroindolizin-7-yl]-1-(4-methylphenylsulfonyl)indole (8, 21 mg, 51.2%) was obtained from 6[(7-R,S)(8a-R,S)-7-hydroxyoctahydroindolizin-7-yl]-1H-indole (example 5(A), 6, 25.6 mg, 0.1 mmoles) and toluenesulfonyl chloride (57 mg, 0.3 mmoles) with 1M NaN((TMS)$_2$ (3004, 0.3 mmoles) in THY (2 mL) at RT.

In a like manner the following compounds are prepared from the intermediates described in example 5 and toluene sulphonyl chloride treated under the conditions described above.
(b) 6-[1-hydroxyhexahydro-1H-pyrrolizine-1-ol-6-yl]-1-(4-methylphenylsulfonyl)indole
(c) 6-[2-hydroxyoctahydro-2H-quinolizine-6-yl]-4-methylphenylsulfonyl)indole
(e) 6-[9-hydroxydecahydropyrido(1,2-a) azepine-6-yl]-1-(4-methylphenylsulfonyl)indole C) conversion of 6->7

The hydroxyl intermediate, prepared as described in example 5A (20 mg, 0.078 mmoles) was mixed with THF (1 ml) and TFA (0.2 ml) and heated at 60–70° C. until TLC showed no starting material left. The reaction mixture was quenched with silica gel and purified by column chromatography with 2–5% of MeOH (2MNH$_3$) in CH$_2$Cl$_2$ to yield:
(a) 6-[(8a-R,S)-1,2,3,5,6,8a-Hexahydroindolizin-7-yl]-1H-indole (7a, 10.5 mg, 56%) and
(b) 6-[(8a-R,S)1,2,3,5,8,8a-Hexahydroindolizin-7-yl]-1H-indole (7b, 4.8 mg, 25.5%)
D) conversion of 7->9

6[(8a-R,S)— 1,2,3,5,6,8a-Hexahydroindolizin-7-yl]-1-naphthylsulfonyl-indole (9) (56.8 mg, 66.7%) was obtained from 6[(8a-R,S)-1,2,3,5,6,8a-Hexahydroindolizin-7yl]-1H-indole (7a, 47.6 mg, 0.2 mmoles) and 1-naphthalenesulfonyl chloride (62.7 mg, 0.3 mmoles) with 1M NaN((TMS)$_2$ (300 µL, 0.3 mmoles) in THF (3 mL) at RT.
(E) conversion of 7a/7b->10/11

6-[(8a-R,S)-1,2,3,5,6,8a-Hexahydroindolizin-7-yl]-1H-indole, obtained as described in Example 5C(a) (7a, 35 mg, 0.147 mmoles), was mixed with 10% Pd/C (45 mg) in ethanol and stirred under $H_2$ at room temperature overnight. The reaction mixture was filtered through celite and concentrated, yielding 35 mg of 6[(7-R,S)(8a-R,S)-Octahydroindolizin-7-yl]H-indole (10/11) as a mixture of two diastereomers (98.7%). The isomers were separated by column chromatography with 2% methanol (2M, NH$_3$) in dichloromethane.
(F) Conversion of 9->12/13

6-[(7-R,S)(8a-R,S)-Octahydroindolizin-7-yl]-1-naphthylsulfonyl-indole (12, 9.3 mg, 20% and 13, 2.5 mg, 5.5%) were obtained from 9 (45 mg, 0.105 mmoles) with 10% Pd/C(30 mg) in methanol(2 ml) under $H_2$.

In a like manner, the corresponding indazole compounds are prepared using 6-bromoindazole in conversion A) and following the synthetic procedures described above for indole.

Example 6

Binding Activity

All compounds were evaluated in vitro for their 5-HT$_6$ receptor binding affinity. The assay protocol entails the incubation of membranes, prepared from HEK293 cells expressing the human 5-HT$_6$ subtype of receptor, with $^3$H-LSD and using clozapine, a typical 5-HT$_6$ receptor antagonist, as a standard (for cloning and characterization of the human 5-HT$_6$ receptor see Kohen, et al. J. Neurochemistry, 66, 1996: 47–56). Specific concentrations of the test compounds were incubated with the radioligand (3H-LSD) and the receptor affinity (K in nM) was determined. Particularly, increasing levels of the test compound were incubated with the radioligand and the membrane homogenates prepared from the recombinant cells. After a 60 minute incubation at 37° C., the incubation was treated by vacuum filtration. The filters were washed with buffer and the filters were counted for radioactivity using liquid scintillation spectrometry. The affinity of the test compound for the 5-HT$_6$ receptor was determined by computer-assisted analysis of the data and determining the amount of the compound necessary to inhibit 50% of the binding of the radioligand to the receptor. Concentrations ranging from $10^{-11}$ M to $10^{-5}$ M of the test compound were evaluated. For comparison, the affinity of clozapine for the 5-HT$_6$ receptor (Ki about 3 nM) was used as a standard.

In general, all of the compounds tested above were found to be very potent at the 5-HT$_6$ receptor with K$_i$s less than 10 nM. In the case of the bicyclopiperazines, the 5,6-bicyclopiperazines were more potent than their corresponding 6,6-bicyclopiperazine. The compound of example 4a, for instance, exhibited a $K_i$=0.2 nM. Similarly, both isomers of Example 5F demonstrated sub-nanomolar 5-HT$_6$ receptor affinity ($K_i$ of 0.8 nM and 0.7 nM, respectively).

Example 7

Biological Activity

The antagonist property of the compounds at the human 5-HT$_6$ receptors was determined by testing their effect on cAMP accumulation in stably transfected HEK293 cells. Binding of an agonist to the human 5-HT$_6$ receptor will lead to an increase in adenyl cyclase activity. A compound that is an agonist will show an increase in cAMP production and a compound that is an antagonist will block the agonist effect Human 5-HT$_6$ receptors were cloned and stably expressed in HEK293 cells. These cells were plated in 6 well plates in DMEM/F12 media with 10% fetal calf serum (FCS) and 500 ug/mL G418 and incubated at 37° C. in a CO$_2$ incubator. The cells were allowed to grow to about 70% confluence before initiation of the experiment. On the day of the experiment, the culture media was removed, and the cells were washed once with serum free medium (SFM). Two mL of SFM+IBMX media was added and incubated at 37° C. for 10 min. The media were removed and fresh SFM+IBMX media containing various compounds, and 1 uM serotonin (as antagonist) were added to the appropriate wells and incubated for 30 min. Following incubation, the media were removed and the cells were washed once with 1 mL of PBS (phosphate buffered saline). Each well was treated with 1 mL cold 95% ethanol and 5 mM EDTA (2:1) at 4° C. for 1 hour. The cells were then scraped and transferred into Eppendorf tubes. The tubes were centrifuged for 5 min at 4° C., and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 uL, peroxidase-labeled cAMP to the sample (100 uL) preincubated with the antiserum (100 uL) for 2 hours at 4° C. Following 1 hour incubation at 4° C., the unbound ligand is separated by a simple washing procedure. Then an enzyme substrate, trimethylbenzidine (1), is added and incubated at room temperature for 60 min. The reaction is stopped by the addition of 100 uL 1.0 M sulphuric acid and the resultant color read by a microtitre plate spectrophotometer at 450 nM within 30 minutes.

In the functional adenylyl cyclase assay, the compound of example 4a was found to be a competitive antagonist (IC$_{50}$=7.2 nM) with good selectivity over a number of other receptors including other serotonin receptors such as 5-HT$_{1A}$ and 5-HT$_7$.

We claim:
1. A compound of Formula I:

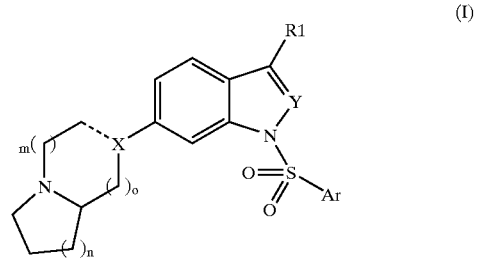

(I)

wherein:
R1 is H or C$_{1-4}$-alkyl;
... X is —CH, —C—O=R3, =C, or —N;
... Y is C-R2 or N
R2 is H or C$_{1-4}$alkyl;
R3 is H, or —C(O)-R4
R4 is H or a labile prodrug group alkyl
n is 1 or 2;
m and o are 1;
and Ar is an aryl or heteroaryl group selected from the group consisting of pyridyl, thienyl, quinolinyl, pyrimidyl, furyl, thiazolyl, oxazolyl, and imidazolyl and which aryl or heteroaryl group is optionally substituted with 1–3 substituents.

2. A compound according to claim 1, wherein Y is C-R2.
3. A compound according to claim 1, wherein R2 is H.
4. A compound according to claim 1, wherein R1 is H.
5. A compound according to claim 1, wherein R3 is H.
6. A compound according to claim 1, wherein Ar is aryl.
7. A compound according to claim 6, wherein Ar is phenyl.
8. A compound according to claim 6, wherein Ar is naphthyl.
9. A compound according to claim 8, wherein Ar is 1-naphthyl.
10. A compound according to claim 6, wherein Ar is phenyl substituted by one or two substituents selected from C$_{1-4}$alkyl and halo.
11. A compound according to claim 10, wherein Ar is 4-methyl-phenyl.
12. A compound according to claim 10, wherein Ar is 2,4-difluoro-phenyl.
13. A compound according to claim 1, wherein X is —CH.
14. A compound according to claim 13, wherein n is 1.
15. A compound according to claim 13, wherein n is 2.
16. A compound according to claim 1, wherein X is N.
17. A compound according to claim 16, wherein n is 1.
18. A compound according to claim 16, wherein n is 2.
19. A compound according to claim 1, selected from
6-[6,5-Bicyclopiperazinyl]-1-[1-naphthylenesulphonyl]indole;
6-[6,5-Bicyclopiperazinyl]-1-[toluenesulphonyl]indole;
6-[6,6-Bicyclopiperazinyl]-1-[1-naphthylenesulphonyl]indole;
6-[6,6-Bicyclopiperazinyl]-1-[p-toluenesulphonyl]indole;
6-[6,6-Bicyclopiperazinyl]-1-[2-naphthylenesulphonyl]indole;
6-[6,5-Bicyclopiperazinyl]-1-[2,4-difluorobenzenesulphonyl]indole;
6-[6,6-Bicyclopiperazinyl]-1-[1-bezenesulphonyl]indole;
6-[6,6-Bicyclopiperazinyl]-1-[o-toluenesulphonyl]indole;

6-[(8a-R,S)-1,2,3,5,6,8a-Hexahydroindolizin-7-yl]-1-naphthylsulfonyl-indole;

6-[(7-R,S)(8a-R,S)-Octahydroindolizin-7-yl]-1-naphthylsulfonyl-indole; and

6-[(7-R,S)(8a-R,S)-7-hydroxyoctahydroindolizin-7-yl]-1-(4-methylphenylsulfonyl) indole.

20. A compound according to claim 19, selected from

6-[6,5-Bicyclopiperazinyl]-1-[1-naphthylenesulphonyl] indole;

6-[6,6-Bicyclopiperazinyl]-1-[1-naphthylenesulphonyl] indole;

6-[(8a-R,S)-1,2,3,5,6,8a-Hexahydroindolizin-7-yl]-1-naphthylsulfonyl-indole; and 6-[(7-R,S)(8a-R,S)-Octahydroindolizin-7-yl]-1-naphthylsulfonyl-indole.

21. The compound 6-[6,5-Bicyclopiperazinyl]-1-[1-naphthylenesulphonyl]indole.

22. A pharmaceutical composition comprising a pharmaceutically acceptable carrier and therapeutically effective amount of a compound according to claim 1.

23. A method effective to treat a subject having a medical condition, disease or disorder for which a 5-HT$_6$ receptor antagonist is indicated, and being selected from schizophrenia, and depression, the method comprising the step of administering to the subject a pharmaceutical composition according to claim 22.

\* \* \* \* \*